(12) United States Patent
Laue et al.

(10) Patent No.: US 6,630,540 B2
(45) Date of Patent: Oct. 7, 2003

(54) COVULCANIZABLE ANTI-AGING AGENTS

(75) Inventors: Christian Laue, Monheim (DE); Markus Oberthür, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 82 days.

(21) Appl. No.: 09/850,511

(22) Filed: May 7, 2001

(65) Prior Publication Data

US 2002/0006994 A1 Jan. 17, 2002

(30) Foreign Application Priority Data

May 11, 2000 (DE) .......................................... 100 22 950

(51) Int. Cl.$^7$ ..................... C08C 19/22; C07C 211/09
(52) U.S. Cl. ..................... 525/332.7; 564/430; 564/434
(58) Field of Search .......................... 524/81, 194, 326, 524/233, 248; 564/430, 434; 525/332.7

(56) References Cited

U.S. PATENT DOCUMENTS

| 4,633,016 A | * 12/1986 | Buysch et al. ............... 564/154 |
| 5,574,118 A | 11/1996 | Olivier ....................... 526/281 |

FOREIGN PATENT DOCUMENTS

| DE | 197 18 288 | 11/1997 |
| EP | 0 308 992 | 3/1989 |
| EP | 0 310 140 | 4/1989 |
| JP | 61-111343 | 5/1986 |
| WO | 97/14678 | 4/1997 |

OTHER PUBLICATIONS

Rubber Chem. Technol. 46 (1) (month unavailable) 1973 pp. 96–105, Preparation and Activity of Polymerizable Antioxidants for Emulsion Rubbers, R. H. Kline and J. P. Miller.

Rubber Chem. Technol. 50 (4) (month unavailable) 1977, pp. 650–659, Incorporation of Antioxidant Groups into polydienes. II. Via Free–Radical Reactions of Phenol– or Amine– Substituted Sulfur Compounds, A. H. Weinstein.

Gummi, Asbest, Kunsts 40, (month unavailable) 1987, pp. 238–258, Schutzmittel fur Langzeit–wirkung in Kautschuk, Dr. Hermann Fries.

Gummi, Fasern, Kunsts, 43 (3), (month unavailable) 1990–pp. 138–144, Einsatz von träger–gebundenen Wirkstoffen für die Gummiherstellung, Werner W. Schunk.

Die Angewandte Makromolekulare Chemie 211, 1993 (month unavalilable) pp. 165–194 (Nr. 3694), Immobilisierbare Stabilisatoren für EPDM–Kautschuk, Dietrich Braun, Rainer Rettig, Wolfgang Rogler.

Polymer Degradation and Stability 4, 1982 (month unavailable) pp. 279–285, Mechanisms of Antioxidant Action: Activity of Sulphur–Linded Bound Antioxidants in Natural Rubber. G. Scott & S. M. Tavakoli.

* cited by examiner

*Primary Examiner*—Robert D. Harlan
(74) *Attorney, Agent, or Firm*—Joseph C. Gil; Noland J. Cheung; Jennifer R. Seng

(57) ABSTRACT

This invention relates to covulcanizable anti-aging agents which can be produced by the reaction of p-phenylenediamines, which are optionally substituted, and/or of sterically hindered phenols, with bifunctional alkyl, aryl and/or aralkyl compounds and by subsequent reaction of the products thus obtained with sulfur and/or sulfur donor compounds. The anti-aging agents according to the present invention maintain their efficacy over a long period of time and are distinguished in particular by the fact that in practice, they are hardly extracted from the vulcanized products by water, by oil and/or petrol, or by hydraulic fluids.

18 Claims, No Drawings

COVULCANIZABLE ANTI-AGING AGENTS

FIELD OF THE INVENTION

The present invention relates to covulcanizable anti-aging agents, which are capable of imparting long-lasting protection from thermal aging and fatigue, and from aging due to the effects of oxygen, to vulcanized rubber products. The anti-aging agents according to the present invention are also distinguished by the fact that they are practically hardly extracted from the vulcanized products by water, by oil and/or petrol, or by hydraulic fluids.

BACKGROUND OF THE INVENTION

It is known that vulcanized rubber products can be protected by anti-aging agents from environmental effects, which destroy these vulcanized products. Thus, for example, known phenolic, aminic, sulfur-containing or phosphorus-containing anti-aging agents are added in order to improve the thermal stability and shelf life of vulcanized rubber products. These are described in greater detail in Ullmann's Enzyklopädie der technischen Chemie, Volume 8, page 19 et seq., for example.

Moreover, it is known that the volatility of anti-aging agents can be reduced by depositing them on support materials and/or by providing them with reactive groups so that they are copolymerized during the production of the rubber, or by depositing them by grafting on the rubber to be protected before vulcanization. Anti-aging agents which are modified in this manner are described, for example, in JP 61 111 343, by W. Schunk, Gummi, Fasern, Kunstst. 43 (3), (1990), 138–144, by R. H. Kline and J. P. Miller, Rubber Chem. Technol. 46 (1), (1973), 96–105, in EP 466 263, DE 19 718 288 and EP 120 801, by H. Fries, Gummi, Asbest, Kunstst. 40. (1987), 238–258, by D. Braun, R. Rettig, W. Rogler, Angew. Makromol. Chem. 211, (1993), 165–194, in DE-A 3 430 510, by G. Scott and S. M. Tavakoli, Polym. Degrad. Stab. 4 (4), (1982), 279–285, and by A. H. Weinstein, Rubber Chem. Technol. 50 (4), (1977), 650–659.

The disadvantages of the anti-aging agents for vulcanized rubber products which have been known hitherto is first, their volatility or ease of extraction, and second, particularly for modified anti-aging agents, is that they are added during the polymerization of the monomers for the production of the rubber are and, therefore, have an adverse effect on the polymerization reaction (e.g. they reduce the rate of reaction).

SUMMARY OF THE INVENTION

The object of the present invention, is thus to provide an anti-aging agent which first does not have an adverse effect on the polymerization of monomers and which second, does not exhibit the volatility and ease of extraction of known anti-aging agents, without the efficacy of the anti-aging agents according to the present invention being reduced compared with that of anti-aging agents which were known hitherto.

The present invention relates to covulcanizable anti-aging agents, which can be produced by the reaction of p-phenylenediamines, which are optionally substituted, and/or of sterically hindered phenols, with bifunctional alkyl, aryl and/or aralkyl compounds and subsequent reaction of the products thus obtained with sulfur and/or with sulfur donor compounds.

DETAILED DESCRIPTION OF THE INVENTION

Suitable p-phenylenediamines, which are optionally substituted, are those of formula (I):

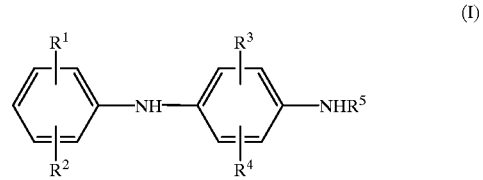

where $R^1$ to $R^4$ are identical or different and represent hydrogen, a straight chain or branched $C_1$–$C_{12}$-alkyl, a $C_1$–$C_{12}$-alkoxy, a $C_1$–$C_{12}$-alkyl-thio, a $C_1$–$C_{12}$-alkyl-amino, a di-($C_1$–$C_{12}$-alkyl)-amino, benzyl, 1,1-di-methylbenzyl or phenyl, and $R^5$ represents hydrogen, phenyl, a $C_6$–$C_{12}$-aryl, a $C_1$–$C_{12}$-heteroaryl or a $C_1$–$C_{12}$-alkyl.

$C_1$–$C_{12}$-alkyl radicals are to be understood to mean all linear, cyclic or branched alkyl radicals containing 1 to 12 C atoms which are known to one skilled in the art, such as methyl, ethyl, n-propyl, i-propyl, n-butyl, t-butyl, n-pentyl, i-pentyl, neo-pentyl, n-hexyl, cyclohexyl, i-hexyl, heptyl, octyl, nonyl, decyl, undecyl and dodecyl radicals, which may in themselves be substituted.

Suitable substituents include halogen, nitro and hydroxyl groups, and also include $C_1$–$C_{12}$-alkyl, $C_1$–$C_{12}$-alkoxy, $C_5$–$C_{12}$ cycloalkyles $C_6$–$C_{12}$-aryl and $C_1$–$C_{12}$-heteroaryl radicals, such as benzyl, trimethylphenyl, ethylphenyl, chloromethyl, chloroethyl or nitromethyl radicals.

$C_1$–$C_{12}$-alkoxy radicals are to be understood to mean all linear, cyclic or branched alkoxy radicals containing 1 to 12 C atoms which are known to one skilled in the art, such as methoxy, ethoxy, n-propoxy, i-propoxy, n-butoxy, i-butoxy, t-butoxy, n-pentoxy, i-pentoxy, neopentoxy and hexoxy radicals, which may themselves be substituted by the aforementioned substituents.

$C_5$–$C_{12}$-cycloalkyl radicals are to be understood to mean all mono- or polynuclear cycloalkyl radicals containing 5 to 12 C atoms which are known to one skilled in the art, such as cyclopentyl, cyclohexyl, cycloheptyl, cyclooctyl and cyclononyl radicals, which may themselves be substituted by the aforementioned substituents.

$C_6$–$C_{12}$-aryl radicals are to be understood to mean all mono- or polynuclear cycloalkyl radicals containing 6 to 12 C atoms which are known to one skilled in the art, such as phenyl or naphthyl radicals, which may themselves be substituted by the aforementioned substituents.

$C_1$–$C_{12}$-heteroaryl radicals are to be understood to mean all mono- or polynuclear heteroalkyl radicals which are known to one skilled in the art, and which in addition to 1 to 12 C atoms also contain heteroatoms such as N, S, O and/or P in their aromatic ring system, e.g. pyridinyl, triazinyl, furyl, thienyl, thiazolyl, thiazinyl, pyrrolyl and quinolinyl, which themselves may be substituted by the aforementioned substituents.

A preferred embodiment of p-phenylenediamines of formula (I) are those in which $R^1$ to $R^4$ represent hydrogen, methyl, ethyl, propyl, t-butyl, 2-propyl, 2-butyl, methoxy, ethoxy, cyclohexyl, benzoyl, phenyl, naphthyl, chlorophenyl or toluyl, and $R^5$ represents hydrogen, 2-propyl, 1,3-dimethylbutyl or cyclohexyl.

A preferred embodiment of sterically hindered phenols are those of general formula (II):

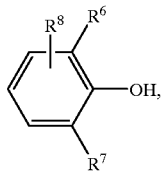

(II)

in which $R^6$ and $R^7$ are identical or different and represent hydrogen, a straight chain or branched $C_1$–$C_{12}$-alkyl, a bridging $C_1$–$C_{12}$-alkenyl, or di(cyclopentadiene)diyl, and $R^8$ has the meaning of $R^6$ or $R^7$, or represents a $C_6$–$C_{12}$-arylthio, a branched or straight chain $C_1$–$C_{12}$-alkylthio, or a grouping of formula:

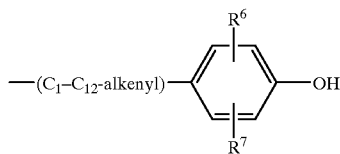

with the aforementioned meaning of $R^6$ or $R^7$.

The sterically hindered phenols which are preferably used are those in which $R^6$ and $R^7$ represent hydrogen, methyl, ethyl, 2-propyl, tert.-butyl, 1,1-dimethylpropyl, cyclohexyl, cyclopentyl, methylene, ethylene, butylene or iso-butylene, and $R^8$ denotes hydrogen, methyl, tert.-butyl, 2-propyl, 2-butyl, cyclohexyl, cyclopentyl, nonylthio, dodecylthio or cyclohexylthio.

The p-phenylenediamines and sterically hindered phenols which are used for the production of the anti-aging agents according to the present invention are known to one skilled in the art and are described, for example, by J. G. Gillick, Elastomerics, 120 (8), (1988), 17–19, by K. B. Chakraborty, G. Scott and J. Rekers, Polym. Prepr. (Am. Chem. Soc., Div. Polym. Chem.) 26 (2), (1985), 31, by J. A. Kuczkowski and J. G. Gillick, Rubber Chem. Technol. 57 (3), (1984), 621–651, by G. Scott, Polym. Prepr. (Am. Chem. Soc., Div. Polym. Chem.), 25 (1), (1984), 62–63 and by G. Scott, Gummi, Asbest, Kunstst. 31 (12), (1978), 934–938, 940, 966.

Compounds of formulae (III), (IV) and (V) can be used as bifunctional alkyl, aryl and/or aralkyl compounds:

 (III)

 (IV)

 (V)

in which $F_1$ represents chlorine, bromine, iodine, a hydroxyl, a carbonyl, a carboxyl, an olefin, an alkyne, a sulfate, a sulfonate, a phosphate, a carbonate, an isocyanate or an isothiocyanate, and $F_2$ represents a halogen, an olefin, an alkyne, a phosphate or a thiophosphate, hydrogen sulfide, a di- or trisulfane, or a sulfite or thiosulfate, wherein the alkanediyl group contains 1 to 30 carbon atoms, can optionally be singly- or multiply-interrupted by hetero atoms, such as oxygen, nitrogen or sulfur, can optionally be substituted by $C_1$–$C_{12}$-alkyl, $C_1$–$C_{12}$-alkyloxy, $C_1$–$C_{12}$-alkyl-thio, $C_1$–$C_{12}$-alkylamino, di-($C_1$–$C_{12}$-alkyl)-amino, benzyl, phenyl or $C_5$–$C_{12}$-cycloalkyl groups, and can be straight chained, branched or cyclic, the aralkanediyl group, as well as the arenediyl group, contains 1 to 30 carbon atoms, can optionally be substituted by $C_1$–$C_{12}$-alkyl, $C_1$–$C_{12}$-alkyloxy, $C_1$–$C_{12}$-alkyl-thio, $C_1$–$C_{12}$-alkyl-amino, di-($C_1$–$C_{12}$-alkyl)-amino, benzyl, 1,1-dimethylbenzyl or phenyl, and can contain one or more heteroatoms of the aforementioned type, and the suffices n and m are identical or different, wherein $1 \leq n \leq 10$ and $1 \leq m \leq 10$.

n is preferably given by $1 \leq n \leq 6$ and m is preferably given by $1 \leq m \leq 4$, with $1 \leq n \leq 3$ and $1 \leq m \leq 3$ being most preferred.

The $F_1$ and $F_2$ radicals in formulae (III) to (V) can be identical or different.

The following are preferred as the functional group $F_1$: chlorine, bromine, hydroxy, olefin, carbaldehyde or ketone groups, and $C_2$–$C_{30}$-carboxylates and derivatives thereof, such as $C_2$-halides, anhydrides, esters, amides, isocyanates, sulfates and sulfonates of $C_{30}$-carboxylic acids.

The following are preferred as the functional group $F_2$: chlorine, bromine, vinyl, allyl, styryl, butanedienyl, cyclopentenyl, cyclohexenyl, cyclooctenyl, cyclooctadienyl, alkynyl, hydrogen sulfide, and di- and trisulfanes.

The preferred alkanediyl groups are: methylene, $C_2$–$C_{30}$-alkanediyl, $C_5$–$C_{20}$-cycloalkanediyl, $C_6$–$C_{30}$-bi-, tri- and tetracycloalkanediyl groups, The preferred aralkanediyl groups are: phenyl or benzyl which are optionally singly- or multiply-substituted by straight chain or branched $C_1$–$C_{12}$-alkyl groups.

The preferred arenediyl groups are: phenylene, naphthylene, triazinylene or pyrimidinylene groups which are optionally singly- or multiply-substituted by straight chain or branched $C_1$–$C_{12}$-alkyl groups.

Examples of compounds of formulae (III) to (V) which are used for the production of the anti-aging agents according to the present invention include $C_2$–$C_{30}$-dihalogenoalkanes, $C_2$–$C_{30}$-halogenoalkenes and -alkynes, $C_2$–$C_{30}$-halogenocarbaldehydes, $C_2$–$C_{30}$-halogenoketones and $C_2$–$C_{30}$-halogenocarboxylic acids, unsaturated $C_3$–$C_{30}$-carbaldehydes, $C_3$–$C_{30}$-ketones or $C_3$–$C_{30}$-carboxylic acids which are singly- or multiply-substituted, and $C_1$–$C_{12}$-alkyl esters, $C_1$–$C_{12}$-alkyl amides, anhydrides and acid halides thereof.

The following are used in particular: allyl chloride, 1,4-dichloro-2-butene, 2,3-dichloro-1-butene, 3,7-dichlorocycloocta-1,5-diene, 3-cyclohexene carbaldehyde, isophorone, phorone, mesityl oxide, acrylic acid, methacrylic acid, crotonic acid, maleic acid, fumaric acid, oleic acid, linoleic acid and linolenic acid, and $C_1$–$C_{12}$-alkyl esters thereof such as methyl, ethyl, propyl, 2-propyl, butyl, 2-butyl, tert.-butyl, 2-ethylhexyl, octyl or dodecyl esters thereof, as well as $C_1$–$C_{12}$-alkyl amides thereof, such as the N-methyl, N-ethyl, N-propyl, N-2-propyl, N-butyl, N-2-butyl, N-tert.-butyl, N-2-ethylhexyl, N-octyl or N-dodecyl carbamides thereof, as well as the corresponding $C_2$–$C_{24}$-dialkyl amides containing the aforementioned $C_1$–$C_{12}$-alkyl amide radicals which can be identical or different.

The aforementioned compounds, which are optionally substituted, can also of course be used in admixture with each other.

According to the present invention, 0.1 to 4, preferably 0.5 to 3, most preferably 1 to 2 mol of bifunctional alkyl and/or aralkyl and/or aryl compounds of formulae (III), (IV), (V) are used per mol of p-phenylenediamines, which are optionally substituted, and/or of sterically hindered phenols.

To produce the covulcanizable anti-aging agents according to the present invention, the reaction product, which is obtained in the manner described above is further reacted with sulfur and/or with sulfur donor compounds.

The sulfur donor compounds, which can be used for the production of the anti-aging agents according to the present invention are compounds which are capable of releasing sulfur during the reaction. These sulfur donors are known to one skilled in the art (see Werner Hofmann, "Kautschuktechnologie", Genter Verlag, Stuttgart 1980, 256–258, for example). Compounds which are suitable for this purpose are those which contain one or more direct sulfur-sulfur bonds, such as $C_1$–$C_{30}$-alkyl di-, tri-, tetra-, penta- and polysulfides or di($C_1$–$C_{30}$-alkylamino)-N-di-, —N-tri-, —N-tetra- and N-polysulfides for example.

The sulfur and/or sulfur donor compounds are added to the reaction product which is obtained in an amount such that 1 to 8 mol, preferably 2 to 6 mol, most preferably 3 to 5 mol of sulfur and/or sulfur donor compound are used for each functional group $F_2$. The molar amounts of sulfur to be used are defined here as ⅛ mol $S_8$ (cyclooctasulfur).

As mentioned above, the substituted p-phenylenediamines and sterically hindered phenols can be used in admixture with each other. The most favorable mixture ratio can easily be determined by preliminary tests and depends, for example, on the requisite physical properties of the anti-aging agents. The same applies to the mixture of bifunctional alkyl, aralkyl and aryl compounds which is optionally used, and to the mixtures of sulfur and sulfur-containing compounds which are used.

The reaction of the p-phenylenediamines and/or sterically hindered phenols with the bifunctional alkyl, aralkyl or aryl compounds is usually conducted in the presence of inert, organic solvents.

Examples of suitable inert, organic solvents include: aliphatic or aromatic hydrocarbons which may optionally be substituted with alkyl, alkoxy, halogen, nitro, amino or sulfo groups, as well as aliphatic or aromatic ethers, amines and sulfides.

The following are preferably used as solvents: alkylbenzenes, xylene and petrol of the types, which are known for purposes such as this.

The aforementioned reaction can also, of course, be conducted without a solvent, for example in the melt or in an excess of bifunctional compounds of formulae (III), (IV), and (V) which are present in liquid form.

The most favorable amount of solvent to be used can easily be determined by appropriate preliminary tests.

The first reaction step for the production of the anti-aging agents according to the present invention is usually conducted at temperatures of −20 to +200° C., preferably at 40 to 140° C.

If the first reaction step is conducted with an excess of bifunctional alkyl, aryl and/or aralkyl compounds, the excess of these compounds is distilled off before further reaction is effected with sulfur and/or sulfur-containing or sulfur donor compounds. When an inert, organic solvent is used, it can remain in the reaction product.

The reaction product, which is obtained in the first reaction step is reacted with sulfur and/or with sulfur-containing compounds at temperatures of about 40 to 200° C., preferably at 110 to 160° C., most preferably at 130 to 150° C.

The production of the anti-aging agents according to the present invention by the reaction described above can, of course, be speeded up by suitable catalysts. Examples of suitable catalysts for the first reaction step include: Lewis acids, such as aluminum, zinc, tin, titanium, iron or boron halides, Brönsted acids such as sulfuric and sulfonic acids, hydrochloric acid or phosphoric acid, and also bases such as amines or metal hydroxides, for example sodium, potassium and calcium hydroxides and the aqueous solutions thereof which are known for purposes such as these.

Examples of suitable catalysts for the second reaction include: ammonia, $C_1$–$C_{36}$-alkyl amines, $C_2$–$C_{40}$-dialkyl amines and ammonium salts thereof, hydrogen sulfide, di-, tri- and tetrasulfanes and $C_1$–$C_{36}$-alkyl or $C_1$–$C_{40}$-dialkyl derivatives thereof, as well as salts of metals of Groups 1, 2 and 12 with $C_1$–$C_{36}$-dithiocarboxylic acids and ($C_1$–$C_{36}$-alkyl amides thereof, such as $C_1$–$C_{36}$-alkyl dithiocarbonates, $C_1$–$C_{36}$-alkyl dithiocarbamates, ($C_1$–$C_{36}$-alkyl)-mercaptothiazole or ($C_1$–$C_{36}$-alkyl)-mercaptobenzothiazoles for example. Other catalysts include salts of metals of groups 1, 2 and 12 with thiosulfuric acids and thiophosphoric acids, with hydrogen sulfide, with di-, tri- and tetrasulfanes, and with selenic, telluric, phosphoric and cyanic acids and hydrogen iodide.

The catalysts are used in customary amounts (0.1 to 10 mol % with respect to one mol of bifunctional compounds of formulae (III), (IV) or (V)).

The anti-aging agent, which is obtained according to the present invention is used as mentioned above for the protection of vulcanized rubber products which are exposed to harmful environmental effects. It is possible, of course, to combine these anti-aging agents with the anti-aging agents which are known to one skilled in the art for the protection of vulcanized rubber products. The most favorable mixture ratio can easily be determined by suitable preliminary tests and depends on the respective purpose of use of the vulcanized products to be protected.

Moreover, it is possible to use the anti-aging agent according to the present invention in admixture with one of the known ozone protection agents in order to achieve improved protection of vulcanized rubber products from ozone. Here also, one skilled in the art can easily determine the most favorable mixture ratio by preliminary tests.

The anti-aging agent according to the present invention is normally used in amounts of 0.5% by weight to 10% by weight, preferably 2% by weight to 5% by weight, with respect to 100 parts of the rubber to be protected.

The rubber compound can also, of course, contain other adjuvant substances for rubber, such as reaction accelerators, thermal stabilizers, light stabilizers, processing aids, plasticizers, tackifiers, foaming agents, colorants, pigments, waxes, extenders, organic acids, retarders, and metal oxides, as well as activators such as triethanolamine, polyethylene glycol or hexanetriol, which are known and which are customary in the rubber industry. These rubber adjuvants are admixed in the customary amounts depending on the intended purpose of use in each case. Examples of customary amounts are 0.1 to 50% by weight with respect to the total amount of rubber used.

Apart from the adjuvant substances mentioned above, known crosslinking agents can be added to the rubber compound, such as sulfur or sulfur donors, and vulcanized production accelerators can be added, such as mercaptobenzthiazoles, benzthiazole sulfenamides, guanidines, thiurams, dithiocarbamates, thioureas and/or thiocarbonates. The vulcanized production accelerators and the aforementioned crosslinking agents are normally used in amounts of 0.1 to 10% by weight, preferably 0.5 to 4% by weight, with respect to the total amount of rubber, which is used in each case.

Vulcanization of rubber compounds containing the anti-aging agents according to the present invention can be effected at the customary temperatures of 100 to 200° C., preferably 130 to 180° C. (optionally under a pressure of 10 to 200 bar).

Further admixture of the rubbers with the other aforementioned rubber adjuvants, crosslinking agents and accelerators can be effected in the usual manner with the aid of suitable mixing units such as rolls, kneaders and compounding extruders.

The rubber blends which are obtained can optionally be compounded and vulcanized in the usual manner, as is described in more detail in the Encyclopedia of Polymer Science and Engineering, Vol. 4, page 66 et seq. (Compounding) and Vol. 17, page 666 et seq. (Vulcanization), for example.

EXAMPLES

Production of covulcanizable anti-aging agents according to the present invention

Compound A

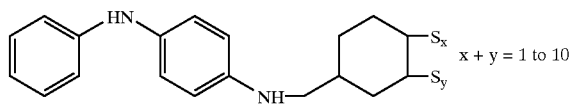

440 g (4 mol) cyclohex-3-ene carbaldehyde were dissolved in 900 ml hexane in a 2 liter four-necked flask fitted with a water trap, and were heated under reflux with stirring. 368 g (2 mol) 4-ADPA (4-aminodiphenylamine) were added, whereupon 34.5 ml of water of reaction were formed over 4.5 hours. After distilling off the solvent and excess aldehyde, the residue was taken up at 50° C. in 500 ml methanol, was treated over 3.5 hours with 110 g (3.0 mol) sodium borohydride added in portions, and was stirred for a further 6 hours at 60° C. After distilling off the solvent, 600 ml toluene and 500 ml water were added to the crude product, and the organic phase was washed twice with 500 ml water and filtered through 50 g sodium sulfate. The solvent was distilled off under the vacuum of a water pump (20 mbar) at 80° C. and the product was rectified by means of 15 cm Vigreux column. 300 g of a wax-like solid with a boiling point of 219° C./0.2 mbar were obtained.

83.7 g (0.3 mol) of the crude product (N-phenyl-N'-(cyclohex-3-enyl)methyl-p-phenylenediamine), 38.4 g (1.2 mol) sulfur and 200 ml xylene were heated for 11 hours under reflux, with stirring. The xylene was distilled off and the residue was isolated as 119.6 g of a black solid. Elemental analysis: S: 28.2%, H: 5.4%, C: 58.5%, N: 7.6%.

Compound B

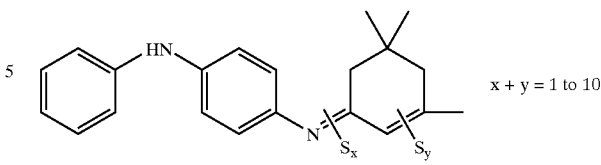

1844 g (1 mol) 4-ADPA (4-aminodiphenylamine) were dissolved in 600 ml xylene with stirring in a 1 liter four-necked flask fitted with a water trap and thermometer, and were heated under reflux with 2 g p-toluenesulfonic acid; 179.7 g (1.3 mol) isophorone were added. 16.5 ml of water separated out over 8 hours. 500 ml water and 50 g $NaHCO_3$ were subsequently added to the reaction mixture, the batch was stirred, the phases were separated in a separating funnel and the organic phase was filtered through 50 g $Na_2SO_4$. After distilling off the volatile constituents (0.2 mbar, 100° C.), the intermediate (a black-brown residue) was recrystallized from 600 ml toluene and 300 ml n-hexane. Yield: 99 g of yellow, crystalline N-phenyl-N'-3,3,5-trimethyl-cyclohex-2-enylene-p-phenylenediamine, m.p.:126–128° C.

15.3 g (0.05 mol) of the above reaction product and 7.4 g (0.23 mol) sulfur were dissolved in 100 ml xylene with stirring and the batch was stirred for 5 hours at 140° C. until TLC: Thin Layer Chromatography (DC: german form of TLC) monitoring indicated that the conversion was almost complete. After distilling off the solvent (70° C., 0.2 mbar), 19.8 g of black, viscous product were obtained.

Compound C

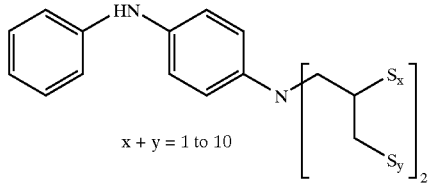

306 g (4 mol) allyl chloride were added drop-wise over 2 hours to a solution of 368 g (2 mol) 4-ADPA and 445.2 g (4.4 mol) triethylamine in 600 ml toluene and the mixture was maintained under reflux for a further 6 hours, whereupon a precipitate was formed. After adding 400 ml toluene and 1 liter of water, the phases were separated. The organic phase was washed twice with 500 ml water each time and was dried over 50 g sodium sulfate. After removing the solvent by distillation, the product was rectified under vacuum to give 435 g of a yellow oil. Boiling point: 160° C./0.15 mbar.

211 g (6.58 mol) sulfur in 500 ml xylene were added in portions at 130° C. over 2 hours to this intermediate (435 g (1.645 mol)). After a further 13 hours at 130–140° C., the reaction mixture was cooled, the solvent was removed under vacuum and the residue was isolated, to give 573.7 g of a dark solid.

Elemental analysis: C: 60.7%, H: 5.2%, N: 8.3%, S: 26.1%

Compound D

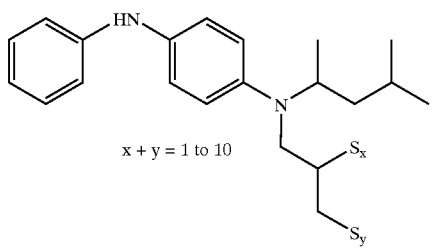

x + y = 1 to 10

246 g (3.6 mol) allyl chloride were added drop-wise over 2.5 hours, with stirring and at the reflux temperature, to a solution of 402 g (1.5 mol) 6PPD (4-(1,3-dimethylbutylamino)-diphenylamine) and 401 g (4 mol) triethylamine in 800 ml toluene, and this mixture was heated to boiling for a further 12 hours. The reaction mixture was mixed with 200 ml toluene and 1 liter of water, the organic phase was washed twice with 1 liter of water each time, the phases were separated and the organic phase was dried over 50 g $Na_2SO_4$. The solvent was removed by distillation and the product was rectified via a small Vigreux column. 385 g of a yellow-brown, oily product mixture were obtained. Boiling point: 163–166° C./0.1 mbar. The crude product (385 g (1.14 mol)) was heated to 130° C. and was treated with 218.9 g (6.84 mol) sulfur, which was added in portions, with stirring, over 4.5 hours. After 12 hours at 135 to 140° C., the reaction mixture was cooled to room temperature. 589 g of a dark product were obtained, which was highly viscous when cold.

Compound E

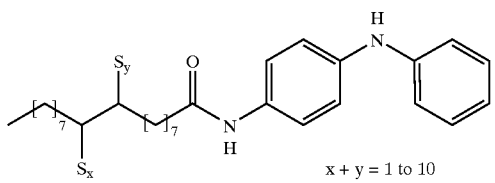

x + y = 1 to 10

148 g (0.5 mol) of methyl oleate, 55.2 g (0.3 mol) 4-ADPA and 2 g sodium methylate were reacted with stirring at 180° C. and for a duration of 9 hours, whereupon 9 ml methanol separated out and were distilled off. The excess methyl oleate was distilled off under high vacuum (230° C., 0.2 mbar). The distillation residue was taken up in 500 ml toluene and 500 ml water and was shaken. After separating the phases in a separating funnel, the organic phase was dried over 30 g sodium sulfate. The toluene was subsequently distilled off under the vacuum from a water pump (20 mbar, 100° C. bath temperature). The residue was isolated: Yield: 116 g of a brown wax.

The reaction product was dissolved in 500 ml xylene, treated with 24.7 g sulfur and maintained under reflux for 3 hours. The solvent was distilled off and the residue was isolated as 120 g of a black solid.

Compound F

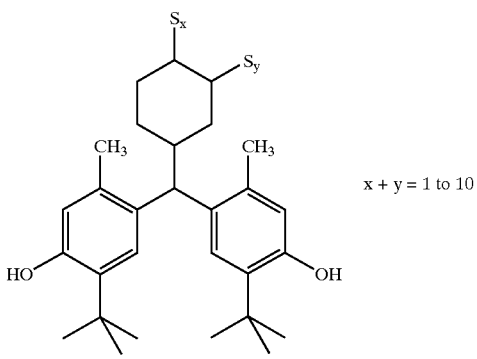

x + y = 1 to 10

A mixture of 669.0 g (3 mol) 6-tert.-butyl-3-methylphenol, 360 ml petrol and 3.58 g concentrated sulfuric acid was heated to 85° C. with stirring. A solution of 165 g (1.5 mol) cyclohex-3-ene-carbaldehyde in 80 ml petrol was added over 5 hours. In the course of this procedure, 27 ml water separated out in the water trap. After filtering the suspension, the filter residue was dried. Yield: 341 g (0.812 mol) of a light grey solid. Melting point: 237–244° C.
21 g (0.05 mol) of the above reaction product cyclohex-3-en-1-ylmethylene-4'4"-bis (2'-tert.-butyl-5'-methylphenol) were dissolved in 20 ml xylene at 115° C. This solution was treated with 9.6 g (0.30 mol) sulfur and was stirred under reflux for 49 hours. The solvent was then distilled off. The residue consisted of 36 g of a brown solid.

Results of application technology investigations

| Compound formulation | |
|---|---|
| TSR 5[1] | 100 |
| Renopal ® 450[2] | 6 |
| Stearic acid[3] | 2 |
| Antilux ® 111[4] | 2 |
| Zinc white RS | 5 |
| Rhenocure ® IS90/G[5] | 2.2 |
| Vulkacit ® CZ[6] | 1.5 |
| Total: | 118.7 |

[1]TSR 5, Weber & Schaer GmbH & Co
[2]Renopal 450, Fuchs Mineralölwerke GmbH
[3]Stearic acid, Henkel KgaA Dehydag Oleogrundstoffe
[4]Antilux 111, Rhein-Chemie Rheinau GmbH
[5]Rhenocure ® IS90/G, Rhein-Chemie Rheinau GmbH
[6]Vulkacit ® CZ, Bayer AG

TABLE 1

| | phr: part per hundred rubber | | | | | |
|---|---|---|---|---|---|---|
| Master batch | 118.7 | 118.7 | 118.7 | 118.7 | 118.7 | 118.7 |
| 6PPD | — | 4 | — | — | — | — |
| A | — | — | 4 | — | — | — |
| B | — | — | — | 4 | — | — |
| C | — | — | — | — | 4 | — |
| D | — | — | — | — | — | 4 |
| Roll: | 2.2 | 2.2 | 2.2 | 2.2 | 2.2 | 2.2 |
| Rhenocure IS 90G | | | | | | |
| Vulkacit CZ/C | 1.5 | 1.5 | 1.5 | 1.5 | 1.5 | 1.5 |
| Test piece | control sample | 6PPD | A | B | C | D |

The rubber compounds were prepared as follows: all the substances listed above, with the exception of Rhenocure® IS90/G and Vulkacit® CZ, were admixed with the rubber matrix in a TPE GK 1.5 E kneader (volume about 1500 ml; temperature=40° C.). Rhenocure® IS90/G and Vulkacit® CZ were subsequently incorporated in the compound on a roll at 40° C. The roll speed was 12 rpm; friction=1.22.

The compounds were thereafter vulcanized to produce rubber sheets (100×100×2 mm) in electrically heated presses (300 bar) at 150° C. until T 90+5 min. was reached on the rheometer curves.

Extraction Tests

The vulcanized products were stored in acidic water at pH 4 and 40° C. After periods of immersion of 7 and 28 days the samples were removed and the total nitrogen content therein was determined by the Kjeldahl method. The nitrogen content represented the sum of the added aminic anti-aging agents according to the present invention and of the 6PPD and customary, amine-containing vulcanization accelerators.

Comparison of the nitrogen contents clearly showed that significant amounts of a conventional anti-aging agent, such as Vulkanox® 4020 for example, were extracted from the vulcanized products after contact with water for only four weeks.

The behavior of vulcanized products which contained anti-aging agents according to the present invention (compounds A to D) was surprisingly different.

After an initial loss of nitrogen, which approximately corresponded to the normal loss of the control sample, the vulcanized products which contained compounds A to D lost hardly any nitrogen or amine.

The amount of aminic (=amine-containing) anti-aging agent contained in the vulcanized products hardly decreased during storage in water.

Even after a longer time of contact with extractive media such as acidic water, the vulcanized products still contained the predominant proportion of the added aminic anti-aging agents according to the present invention. In parallel with this, there was continued protection of the vulcanized products from aging phenomena.

TABLE 2

| Test piece | N content [%] 0 days Extraction period (water) | 7 days Extraction period | 28 days Extraction period |
| --- | --- | --- | --- |
| control sample | 0.53 | 0.52 | 0.51 |
| 6PPD | 0.68 | 0.59 | 0.54 |
| A | 0.63 | 0.59 | 0.58 |
| B | 0.65 | 0.59 | 0.59 |
| C | 0.65 | 0.59 | 0.59 |
| D | 0.68 | 0.61 | 0.6 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing covulcanizable anti-aging agents comprising the step of reacting p-phenylenediamines, which are optionally substituted, and/or of sterically hindered phenols, with bifunctional alkyl, aryl and/or aralkyl compounds to form a reaction product and reacting said reaction product with sulfur and/or with sulfur donor compounds.

2. A process according to claim 1, wherein said p-phenylenediamines are of the formula (I)

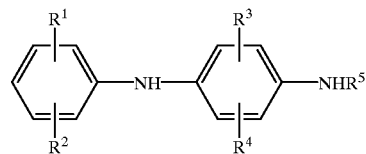

where
R$^1$ to R$^4$ are identical or different and represent hydrogen, a straight chain or branched C$_1$–C$_{12}$-alkyl, a C$_1$–C$_{12}$-alkoxy, a C$_1$–C$_{12}$-alkyl-thio, a C$_1$–C$_{12}$-alkyl-amino, a di-(C$_1$–C$_{12}$-alkyl)-amino, benzyl, 1,1-dimethylbenzyl or phenyl, and
R$^5$ represents hydrogen, phenyl, a C$_6$–C$_{12}$-aryl, a C$_1$–C$_{12}$-heteroaryl or a C$_1$–C$_{12}$-alkyl.

3. A process according to claim 1, wherein the sterically hindered phenols are of the formula (II):

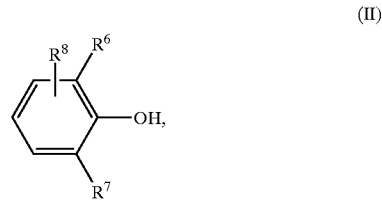

wherein
R$^6$ and R$^7$ are identical or different and represent hydrogen, a straight chain or branched C$_1$–C$_{12}$-alkyl, a bridging C$_1$–C$_{12}$-alkenyl, or di(cyclo-pentadiene)diyl, and
R$^8$ has the meaning of R$^6$ or R$^7$, or represents a C$_6$–C$_{12}$-arylthio, a branched or straight chain C$_1$–C$_{12}$-alkylthio, or a grouping of formula:

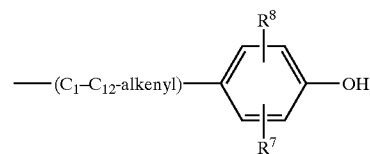

with the aforementioned meaning of R$^6$ or R$^7$.

4. A process according to claim 1, wherein said bifunctional alkyl, aryl and/or aralkyl compounds can be of formulae (III), (IV) and (V):

$(F_1)_n$-alkanediyl-$(F_2)_m$     (III)

$(F_1)_n$-aralkanediyl-$(F_2)_m$     (IV)

$(F_1)_n$-arenediyl-$(F_2)_m$     (V)

wherein
F$_1$ represents chlorine, bromine, iodine, a hydroxyl, a carbonyl, a carboxyl, an olefin, an alkyne, a sulfate, a sulfonate, a phosphate, a carbonate, an isocyanate or an isothiocyanate, and
F$_2$ represents a halogen, an olefin, an alkyne, a phosphate or a thiophosphate, hydrogen sulfide, a di- or trisulfane, or a sulfite or thiosulfate,
wherein
the alkanediyl group contains 1 to 30 carbon atoms, is optionally singly- or multiply-interrupted by heteroatoms, is optionally substituted by a $C_1$–$C_{12}$-alkyl, a $C_1$–$C_{12}$-alkyloxy, a $C_1$–$C_{12}$-alkylthio, a $C_1$–$C_{12}$-alkylamino, a di($C_1$–$C_{12}$-alkyl)-amino, or by benzyl, phenyl or a $C_5$–$C_{12}$-cycloalkyl, and can be straight chain, branched or cyclic, the aralkanediyl group as well as the arenediyl group contain 1 to 30 carbon atoms and can optionally be substituted by a $C_1$–$C_{12}$-alkyl, a $C_1$–$C_{12}$-alkyloxy, a $C_1$–$C_{12}$-alkylthio, a $C_1$–$C_{12}$-alkylamino, a di-($C_1$–$C_{12}$-2-alkyl)-amino, or by benzyl, 1,1-dimethylbenzyl or phenyl, and can contain one or more heteroatoms, and n and m are identical or different, where $1 \leq n \leq 10$ and $1 \leq m \leq 10$.

5. A process according to claim 1, wherein said 0.1 to 4 mol of bifunctional alkyl, aryl and/or aralkyl compounds of formulae (III), (IV) or (V) are used per mol of optionally substituted p-phenylenediamines and/or sterically hindered phenols.

6. A process according to claim 1, wherein the sulfur and/or the sulfur donor compounds are used in amounts such that 1 to 8 mol of sulfur and/or of sulfur donor compounds are used for each functional group $F_2$.

7. Covulcanizable anti-aging agents produced by the reaction of p-phenylenediamines, which are optionally substituted, and/or of sterically hindered phenols, with bifunctional alkyl, aryl and/or aralkyl compounds to form a reaction product and reaction of said reaction product with sulfur and/or with sulfur donor compounds.

8. Covulcanizable anti-aging agents according to claim 7, wherein said p-phenylenediamines are of formula (I):

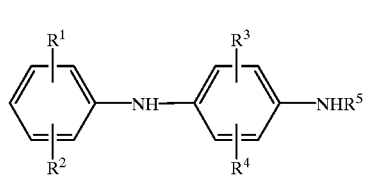

(I)

wherein $R^1$ to $R^4$ are identical or different and represent hydrogen, a straight chain or branched $C_1$–$C_{12}$-alkyl, a $C_1$–$C_{12}$-alkoxy, a $C_1$–$C_{12}$-alkyl-thio, a $C_1$–$C_{12}$-alkyl-amino, a di-($C_1$–$C_{12}$-alkyl)-amino, benzyl, 1,1-dimethylbenzyl or phenyl, and $R^5$ represents hydrogen, phenyl, a $C_6$–$C_{12}$-aryl, a $C_1$–$C_{12}$-heteroaryl or a $C_1$–$C_{12}$-alkyl.

9. Covulcanizable anti-aging agents according to claim 7, wherein the sterically hindered phenols are of formula (II):

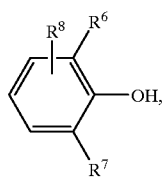

(II)

wherein $R^6$ and $R^7$ are identical or different and represent hydrogen, a straight chain or branched $C_1$–$C_{12}$-alkyl, a bridging $C_1$–$C_{12}$-alkenyl, or di(cyclo-pentadiene)diyl, and $R^8$ has the meaning of $R^6$ or $R^7$, or represents a $C_6$–$C_{12}$-arylthio, a branched or straight chain $C_1$–$C_{12}$-alkylthio, or a grouping of formula:

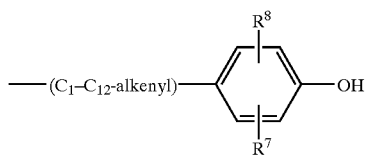

with the aforementioned meaning of $R^6$ or $R^7$.

10. Covulcanizable anti-aging agents according to claim 7, wherein compounds of formulae (III), (IV) and (V) are used as bifunctional alkyl, aryl and/or aralkyl compounds:

$(F_1)_n$-alkanediyl-$(F_2)_m$     (III)

$(F_1)_n$-aralkanediyl-$(F_2)_m$     (IV)

$(F_1)_n$-arenediyl-$(F_2)_m$     (V)

wherein $F_1$ represents chlorine, bromine, iodine, a hydroxyl, a carbonyl, a carboxyl, an olefin, an alkyne, a sulfate, a sulfonate, a phosphate, a carbonate, an isocyanate or an isothiocyanate, and $F_2$ represents a halogen, an olefin, an alkyne, a phosphate or a thiophosphate, hydrogen sulfide, a di- or trisulfane, or a sulfite or thiosulfate, wherein the alkanediyl group contains 1 to 30 carbon atoms, is optionally singly- or multiply-interrupted by heteroatoms, is optionally substituted by a $C_1$–$C_{12}$-alkyl, a $C_1$–$C_{12}$-alkyloxy, a $C_1$–$C_{12}$-alkylthio, a $C_1$–$C_{12}$-alkylamino, a di($C_1$–$C_{12}$-alkyl)-amino, or by benzyl, phenyl or a $C_5$–$C_{12}$-cycloalkyl, and can be straight chain, branched or cyclic, the aralkanediyl group as well as the arenediyl group contain 1 to 30 carbon atoms and can optionally be substituted by a $C_1$–$C_{12}$-alkyl, a $C_1$–$C_{12}$-alkyloxy, a $C_1$–$C_{12}$-alkylthio, a $C_1$–$C_{12}$-alkylamino, a di-($C_1$–$C_{12}$-2-alkyl)-amino, or by benzyl, 1,1-dimethylbenzyl or phenyl, and can contain one or more heteroatoms, and n and m are identical or different, where $1 \leq n \leq 10$ and $1 \leq m \leq 10$.

11. Covulcanizable anti-aging agents according to claim 7, wherein 0.1 to 4 mol of bifunctional alkyl, aryl and/or aralkyl compounds of formulae (III), (IV) or (V) are used per mol of optionally substituted p-phenylenediamines and/or sterically hindered phenols.

12. Covulcanizable anti-aging agents according to claim 7, wherein sulfur and/or the sulfur donor compounds are used in amounts such that 1 to 8 mol of sulfur and/or of sulfur donor compounds are used for each functional group $F_2$.

13. The production of vulcanized rubber products comprising covulcanizable anti-aging agents produced by the reaction of p-phenylenediamines, which are optionally substituted, and/or of sterically hindered phenols, with bifunctional alkyl, aryl and/or aralkyl compounds to form a reaction product and reaction of said reaction product with sulfur and/or with sulfur donor compounds.

14. The production of vulcanized rubber products according to claim 13, wherein, wherein said p-phenylenediamines are of formula (I):

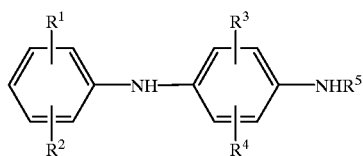

(I)

wherein
- $R^1$ to $R^4$ are identical or different and represent hydrogen, a straight chain or branched $C_1$–$C_{12}$-alkyl, a $C_1$–$C_{12}$-alkoxy, a $C_1$–$C_{12}$-alkyl-thio, a $C_1$–$C_{12}$-alkyl-amino, a di-($C_1$–$C_{12}$-alkyl)-amino, benzyl, 1,1-di methylbenzyl or phenyl, and
- $R^5$ represents hydrogen, phenyl, a $C_6$–$C_{12}$-aryl, a $C_1$–$C_{12}$-heteroaryl or a $C_1$–$C_{12}$-alkyl.

15. The production of vulcanized rubber products according to claim 13, wherein the sterically hindered phenols are of formula (II)

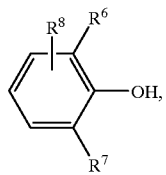

(II)

wherein
- $R^6$ and $R^7$ are identical or different and represent hydrogen, a straight chain or branched $C_1$–$C_{12}$-alkyl, a bridging $C_1$–$C_{12}$-alkenyl, or di(cyclo-pentadiene)diyl, and
- $R^8$ has the meaning of $R^6$ or $R^7$, or represents a $C_6$–$C_{12}$-arylthio, a branched or straight chain $C_1$–$C_{12}$-alkylthio, or a grouping of formula

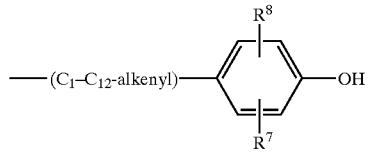

with the aforementioned meaning of $R^6$ or $R^7$.

16. The production of vulcanized rubber products according to claim 13, wherein compounds of formulae (III), (IV) and (V) are used as bifunctional alkyl, aryl and/or aralkyl compounds:

$$(F_1)_n\text{-alkanediyl-}(F_2)_m \quad (III)$$

$$(F_1)_n\text{-aralkanediyl-}(F_2)_m \quad (IV)$$

$$(F_1)_n\text{-arenediyl-}(F_2)_m \quad (V)$$

wherein
- $F_1$ represents chlorine, bromine, iodine, a hydroxyl, a carbonyl, a carboxyl, an olefin, an alkyne, a sulfate, a sulfonate, a phosphate, a carbonate, an isocyanate or an isothiocyanate, and
- $F_2$ represents a halogen, an olefin, an alkyne, a phosphate or a thiophosphate, hydrogen sulfide, a di- or trisulfane, or a sulfite or thiosulfate, wherein
  the alkanediyl group contains 1 to 30 carbon atoms, is optionally singly- or multiply-interrupted by heteroatoms, is optionally substituted by a $C_1$–$C_{12}$-alkyl, a $C_1$–$C_{12}$-alkyloxy, a $C_1$–$C_{12}$-alkylthio, a $C_1$–$C_{12}$-alkylamino, a di($C_1$–$C_{12}$-alkyl)-amino, or by benzyl, phenyl or a $C_5$–$C_{12}$-cycloalkyl, and can be straight chain, branched or cyclic,
  the aralkanediyl group as well as the arenediyl group contain 1 to 30 carbon atoms and can optionally be substituted by a $C_1$–$C_{12}$-alkyl, a $C_1$–$C_{12}$-alkyloxy, a $C_1$–$C_{12}$-alkylthio, a $C_1$–$C_{12}$-alkylamino, a di-($C_1$–$C_{12}$-2-alkyl)-amino, or by benzyl, 1,1-dimethylbenzyl or phenyl, and can contain one or more heteroatoms, and
  n and m are identical or different, where $1 \leq n \leq 10$ and $1 \leq m \leq 10$.

17. The production of vulcanized rubber products according to claim 13, wherein 0.1 to 4 mol of bifunctional alkyl, aryl and/or aralkyl compounds of formulae (III), (IV) or (V) are used per mol of optionally substituted p-phenylenediamines and/or sterically hindered phenols.

18. The production of vulcanized rubber products according to claim 13, wherein sulfur and/or the sulfur donor compounds are used in amounts such that 1 to 8 mol of sulfur and/or of sulfur donor compounds are used for each functional group $F_2$.

* * * * *